United States Patent [19]

Zanon et al.

[11] Patent Number: Plant 5,406

[45] Date of Patent: Feb. 19, 1985

[54] APPLE TREE 'MERAN'

[76] Inventors: Karl Zanon, Via Sibilla 11, Merano, Italy, 39012; Franz Waldner, Via Roma 109, Merano, Italy

[21] Appl. No.: 402,133

[22] Filed: Jul. 26, 1982

[30] Foreign Application Priority Data

May 17, 1982 [IT] Italy ..... 1001NV/82

[51] Int. Cl.[3] ..... A01H 5/00

[52] U.S. Cl. ..... Plt./34

[58] Field of Search ..... Plt./34

*Primary Examiner*—James R. Feyrer

*Attorney, Agent, or Firm*—Neil M. Zipkin

[57] ABSTRACT

The apple variety "MERAN" was created by crossing of the varieties Golden Delicious and Morgenduft.

It differs from the common apple varieties by earlier yield, an excellent natural resistance against diseases, excellent storability, and superior qualitative properties.

6 Drawing Figures

SUMMARY OF THE INVENTION

"MERAN" is a cross of the varieties Golden Delicious and Morgenduft.

The new variety differs in substantial properties from the parent varieties.

HISTORY OF THE VARIETY

Eight years after creation of the new variety by crossing, a period of more intensive observation and investigation of the product was begun in 1974. Since then, the advantages in orchard culture, fruit quality and storability have been verified.

Since 1979, the variety has been grown on several root stocks by asexual reproduction by both budding and grafting, and trees resulting therefrom are true to the parent in all distinguishing characteristics (M 9, M 26, "Grahams Jubiläum Seedling"). Many storage tests were carried out, and the after-storage behaviour was also observed.

BOTANICAL DESCRIPTION OF THE PLANT

Figure 1:
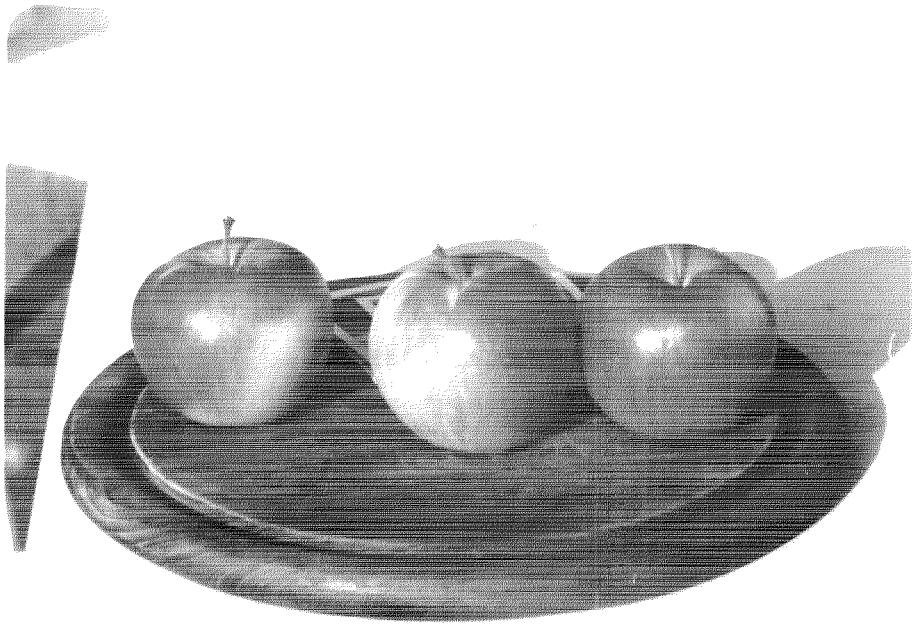
FIG. 1 is a whole fruit of the apple variety "MERAN".
Figure 2:
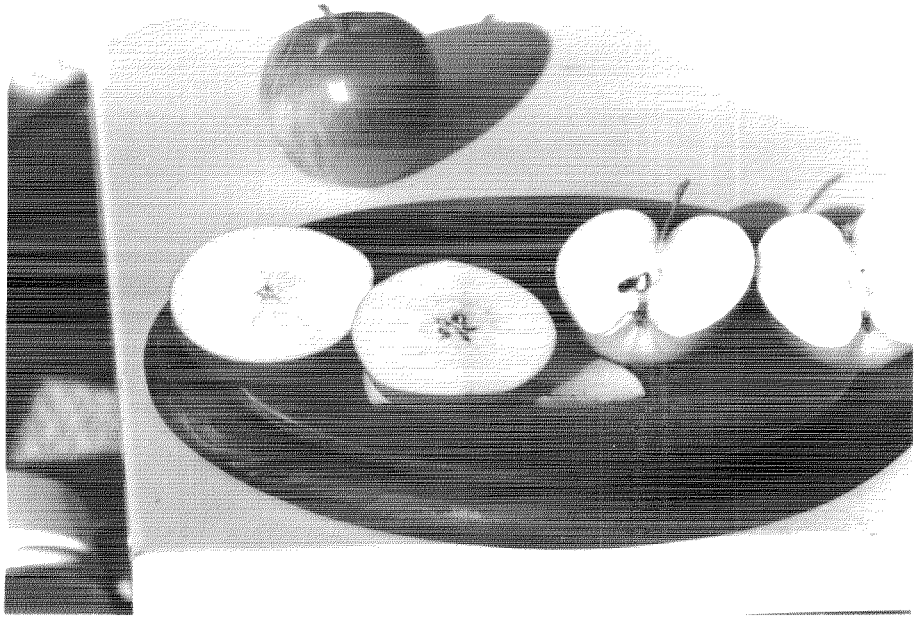
FIG. 2 is a whole fruit and fruit cut into halves by equatorial and longitudinal sections.
Figure 4:
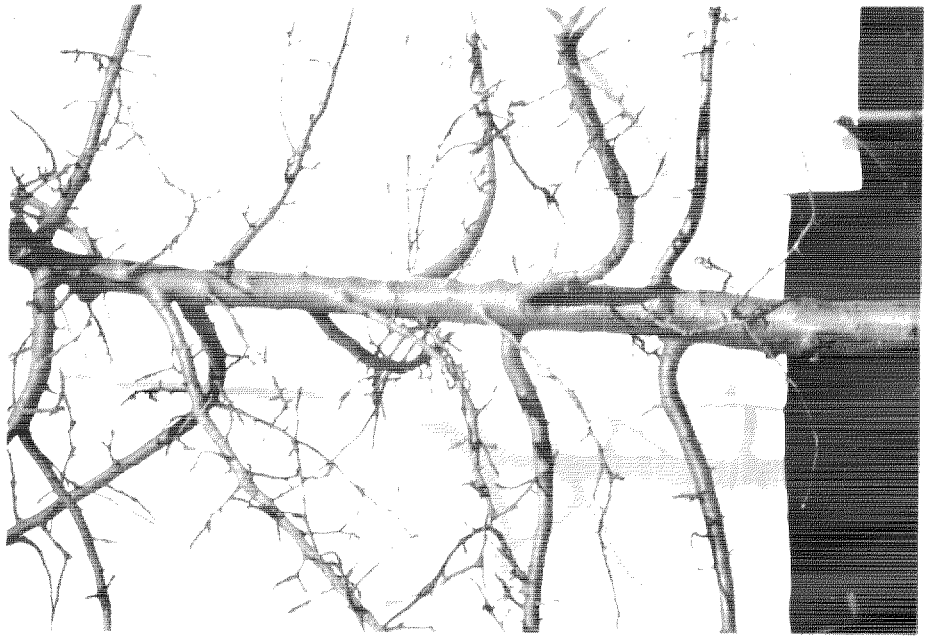
FIGS. 3 and 4 show trees of the apple variety "MERAN" in bearing age.
Figure 3:
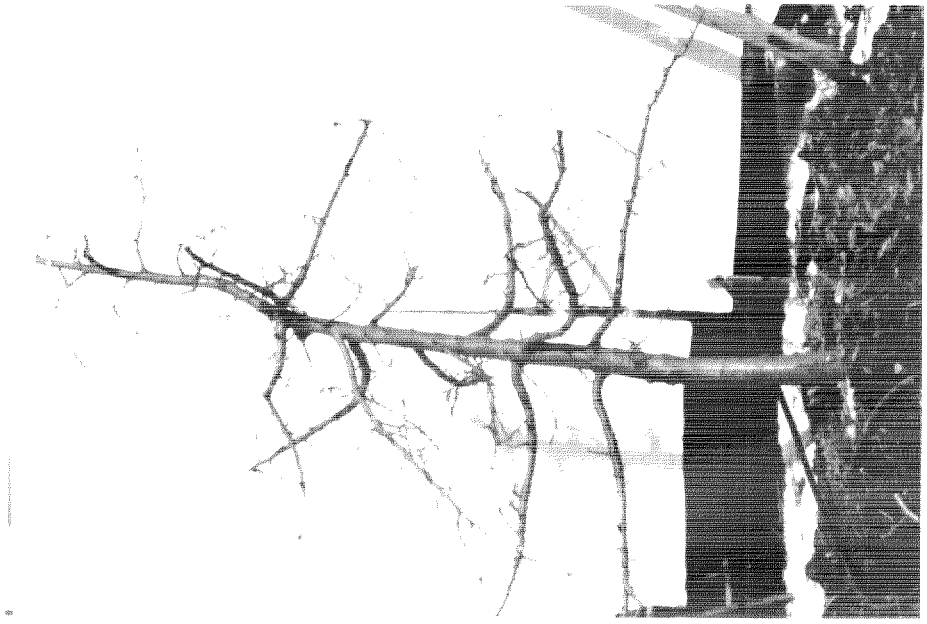
Figure 5:
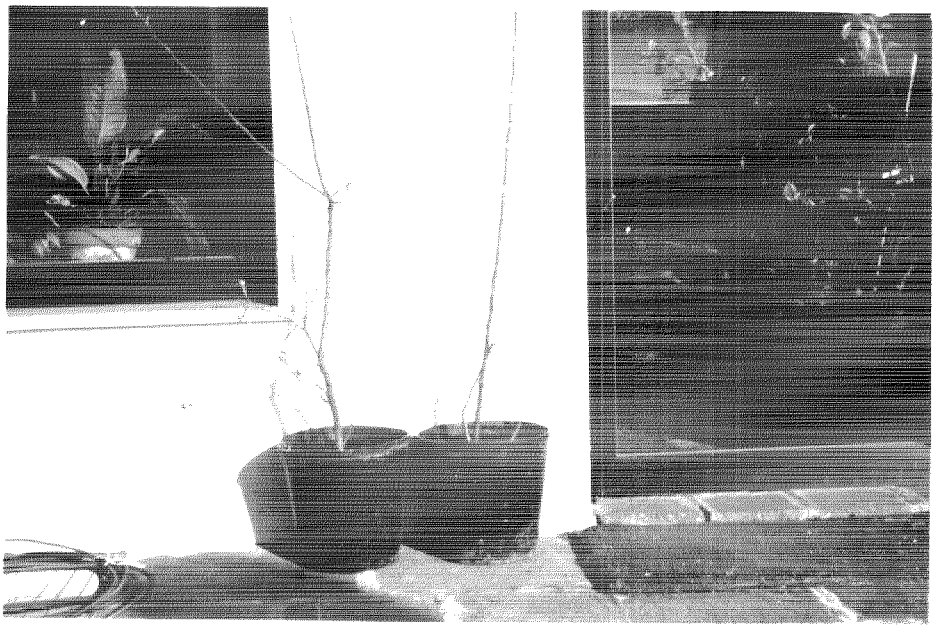
FIGS. 5 and 6 show root-suckers (with roots) of the apple variety "MERAN".
Figure 6:
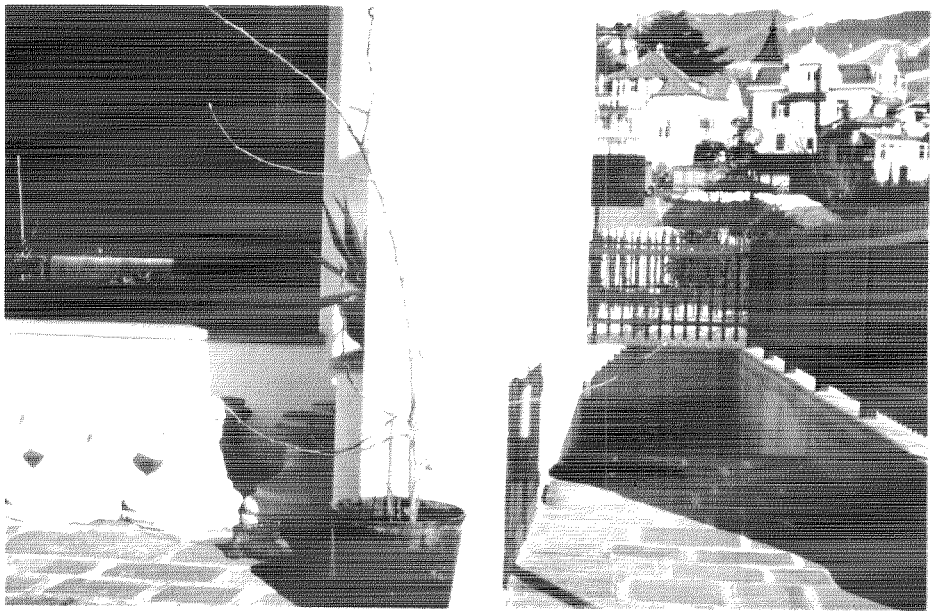

Some specimens of the novel tree which had been marked with an index number have been grown since 1979 at the "Versuchszentrum fur Land- und Forestwirtschaft Laimburg" (Experimental station for agriculture and foresty Laimburg) of the Autonomous Province of South Tyrol, in order to conduct the necessary orchard tests and evaluation (test station of novel cultivations).

PROPERTIES OF THE VARIETY

The root system of the seedling consists of a primary system of some (3-4) large roots, and a secondary system of densely arranged, fine small roots.

The epigeous part shows medium vigor. The crown develops on a central leader with rather low apical dominance and 1-2 series of well-distanced side branches. This means a considerable reduction of labour for pruning and tree formation (binding, bending, spreading).

The variety is not self fertile. The size of the tree on its own stock after 20 years of growth is approximately 3½ meters (medium size). The formation of short sprouts, sprouts and bearing sprouts begins very early. Specifically, two to three series of three to five lateral main branches depart from the central leader at a distance of about 40 to 60 centimeters. Fruiting spurs begin to develop in the second and third year after grafting. First production occurs within 7 to 8 years from asexual reproduction. Habit is compact, similar to spur types. The branch crotch angles vary from 70° to 100° as shown in the drawings.

"MERAN" is a regular bearer. The fruit is slightly fragrant and aromatic. It has double acidity with respect to Golden Delicious while its juiciness and texture is nearer to the Rome Beauty than to the Golden Delicious.

Colouration of the various plant parts is not seen to be particularly a typical of the species per se, but are generally described below:

Wood: Similar to Golden Delicious, but somewhat lighter in colour.

Leaves: Oval, leaf margins serrated. Lighter in colour than Golden Delicious.

Blossoms: Initially dark red, later light pink (Golden Delicious: Light pink first, then almost white).

Blossom Time: Medium (as Golden Delicious).

Pollen: Diploid, requires a pollinator.

Fruit:

*Harvest time.*—In Meran (300 m above sea level) from October 15 to 20 (two weeks after Golden Delicious). Ripeness for consumption: beginning November.

*Size and shape.*—Of medium size, average weight: 140-150 g per fruit (smaller than Golden Delicious), Remarkably uniform. Plattened spherical, roundish.

*Specific gravity.*—Exceeding the specific gravity of Golden Delicous, therefore higher consistency.

*Colour.*—In the ripe fruit, particularly on the sunny side, shining light red, pleasant colour. Basic colour golden yellow as shown in the drawings. Unripe fruit: green.

*Fruit skin.*—Shining, with moderate wax formation, fine, smooth, with distinctly visible lenticels in different density and of different size. The skin is principally free of russeting. Occasionally mild radial russeting in the stem depression.

*Calyx.*—Of medium size, half-open, with well developed leaflets. Stem: long, thin, not breaking off (in contrast to the Golden Delicious).

*Stem depression.*—Deep, narrow, occasionally with mild russeting (see above).

*Core.*—Rather small, heart-shaped, many dark-brown seeds. Fruit pulp: whitish-yellow, of fine, small-cellular structure, very juicy, remaining crisp for up to 7–8 months' storage time and even longer. Broad pulp zone, cut surface not turning brown.

*Taste.*—Finely acidulous. Juice light yellow, transparent. (Golden Delicious: light brown, turbid).

Storability: Excellent up to 7 months in cold store, up to 8 months and even longer in controlled atmospheres.

Shelf-life: Excellent.

Resistance against shocks and other mechanical damages: Excellent. Nearly shock-resistant during sorting, transportation, etc.

OTHER PROPERTIES

Site conditions: As Golden Delicious.

Russeting: Usually missing (in contrast to Golden Delicious). Occasionally mild radial russeting in the stem depression. Somewhat more frequent is a single, needle-thin russeting thread in longitudinal direction of the fruit downwards.

Preharvest fruit drop: Not observed.

Shrinking: Occurring late and to a mild degree if the fruit is stored under natural conditions. Not occuring if the fruit is kept in cold stores.

Rot and fungi: Not observed so far.

Scald: Not observed so far.

Damages due to cold: Not observed so far.

Bitter pit: Not observed so far.

Scab: Not observed so far.

Mildew: Weak contamination.

Pest: As Golden Delicious.

CONCLUSIONS

The new crossbreed "MERAN" differs positively from the parent varieties by many properties which are of great importance for growing, storage and marketing. Of these, the following advantages shall be particularly mentioned:

1. The natural favourable growth and development of the crown due to which considerable savings in labour for pruning and formation are possible.

2. Early entrance into bearing age (1–2 years earlier than the parent varieties).

3. Natural resistance against many diseases and damages (russeting bitter pit, scald, cold damages, scab, etc.)

4. Superior colour, taste and pulp texture.

5. Remarkably good storability and excellent shelf life behaviour up to consumption.

6. Resistance against mechanical influences; this is due to the good pulp texture and other properties of the fruit.

We claim:

1. A new and distinct variety of apple created by crossing of the varieties Golden Delicious and Morgenduft, as shown and described herein.

* * * * *